(12) United States Patent  
Slaker et al.

(10) Patent No.: US 8,397,725 B2
(45) Date of Patent: Mar. 19, 2013

(54) RESPIRATORY TREATMENT DELIVERY SYSTEM

(75) Inventors: Bradley Frank Slaker, Greenfield, MN (US); Ann Gettys, Norman, OK (US); Jennifer Anne Seward, Greenfield, MN (US); Benjamin Olson Valley, Shoreview, MN (US); Ahmed Nazmul Jaffer, Plymouth, MN (US); Jacob Richard Maida, Duluth, MN (US); Fushcia-Ann Elizabeth Hoover, St. Paul, MN (US)

(73) Assignee: DesignWise Medical, Loretto, MN (US)

( * ) Notice: Subject to any disclaimer, the term of this patent is extended or adjusted under 35 U.S.C. 154(b) by 377 days.

(21) Appl. No.: 12/875,229

(22) Filed: Sep. 3, 2010

(65) Prior Publication Data

US 2011/0056489 A1 Mar. 10, 2011

Related U.S. Application Data

(60) Provisional application No. 61/240,036, filed on Sep. 4, 2009.

(51) Int. Cl.
*A61G 10/00* (2006.01)

(52) U.S. Cl. .................................................. 128/205.26

(58) Field of Classification Search ............. 128/202.12, 128/205.26
See application file for complete search history.

(56) References Cited

U.S. PATENT DOCUMENTS

| | | | |
|---|---|---|---|
| 2,418,473 A | 4/1947 | Lambertsen et al. |
| 2,628,803 A | 2/1953 | Krewson |
| 3,680,577 A | 8/1972 | McGeachy |
| 3,786,809 A | 1/1974 | Kitrilakis |
| 4,003,378 A | 1/1977 | Pickering |
| 4,181,129 A | 1/1980 | Cameto et al. |
| D255,833 S | 7/1980 | Crandall |
| D262,653 S | 1/1982 | Koh |
| 4,321,917 A | 3/1982 | Campbell |
| 4,377,161 A | 3/1983 | Whitt |
| 4,413,622 A | 11/1983 | Austin |
| 4,444,183 A | 4/1984 | Heckendorn |
| 4,577,628 A | 3/1986 | Hickmann |
| 4,669,461 A | 6/1987 | Battaglia |
| 4,949,714 A | 8/1990 | Orr |
| 5,509,414 A | 4/1996 | Hok |
| 5,928,189 A | 7/1999 | Phillips et al. |
| 6,065,473 A | 5/2000 | McCombs et al. |
| 6,493,888 B1 | 12/2002 | Salvatini et al. |
| 6,588,420 B1 | 7/2003 | Burch |
| 6,707,933 B1 | 3/2004 | Mariani et al. |
| 6,847,301 B1 | 1/2005 | Olson |
| 2003/0209140 A1 | 11/2003 | Kutt et al. |
| 2007/0151564 A1 | 7/2007 | Sadir et al. |
| 2009/0107501 A1 | 4/2009 | Krieger |

*Primary Examiner* — Jackie Ho
*Assistant Examiner* — Nyca T Nguyen
(74) *Attorney, Agent, or Firm* — William Mitchell IP Clinic

(57) ABSTRACT

Embodiments relate to systems and methods for delivery of oxygen or other treatment gases to a patient without requiring physical contact or enclosure of the patient. Embodiments can include a delivery hood, sensing components, and a gas distribution system including one or more gas delivery ports. Gas delivery ports may be individually controlled based on input from the sensing components to alter the volume and orientation of treatment gas flow directed at a patient. Sensing components can include cameras or other sensors that detect the position of a patient's head, and gas delivery ports may then be controlled to direct treatment gas flow in the direction of the patient's head. Embodiments and methods described thereby allow for efficient oxygen or other gas delivery to a patient without requiring contact or enclosure of the patient.

22 Claims, 13 Drawing Sheets

RESPIRATORY TREATMENT DELIVERY SYSTEM

PRIORITY

This application claims the benefit of U.S. Provisional Application No. 61/240,036, "Overnight Pediatric Oxygen Delivery System," filed Sep. 4, 2009, which is hereby fully incorporated herein by reference.

TECHNICAL FIELD

The invention relates generally to medical care and, more particularly, to oxygen or other therapeutic gas delivery systems, and more particularly to overnight oxygen delivery systems for patients in the home environment.

BACKGROUND

Interstitial lung disease is a group of rare lung diseases in infants and children. These diseases can cause progressive scarring of lung tissue over time, and can also reduce the capability and efficacy of the lungs to transfer oxygen into the bloodstream. Infants and children who suffer blood oxygen levels outside of normal ranges due to these and other similar diseases are often affected with health complications such as stunted growth and pulmonary hypertension. The medical needs of infants and children affected with these diseases vary with the severity of the disease, but in most cases infants and children benefit from systems that provide supplemental oxygen to increase blood oxygen levels. In particular, providing supplemental oxygen to patients while sleeping has been discovered to improve hemoglobin oxygen saturation levels.

Ideally, in cases where supplemental oxygen is beneficial to the patient, systems and methods for delivering oxygen in a home environment are desirable, so that the oxygen treatment can be applied on a continuing basis and not require special visits to a medical facility. Methods of delivering oxygen in the home environment exist; the nasal cannula delivery system and the oxygen mask delivery system are both known in the industry. In addition, oxygen tents and oxygen hoods are known in the industry, although their use is limited to primarily hospital settings.

A typical nasal cannula system as found in the prior art consists of tubing with a specially formed end portion that inserts into a patient's nose. The end portion is typically secured by tape affixed to the patient's skin. A cannula system is advantageous in that it can deliver a precisely controlled amount of oxygen into a patient's lungs. However, when the patients are children or infants, tape burns on their skin can occur as a result of affixing tape directly to the skin. Further, the nasal cannula is often uncomfortable for an infant or child to wear, and such a patient will often struggle and remove the cannula. To remedy the removal problem, arm boards have often been used. Use of an arm board consists of tying the child's arms to a sturdy length of material so the arm is unable to bend at the elbow and thus the infant or child is thereby unable to detach the cannula.

A typical oxygen mask, as found in the prior art, consists of a bulky mask that a patient wears over his nose and mouth. This type of oxygen delivery system is also problematic, as the mask is prone to removal especially when the patient is an infant or child. In addition, both the cannula and oxygen mask systems may require generous amounts of tubing and tape to adequately and reliably transport the oxygen from a storage source to the patient's respiratory system. As a result, a patient can easily become tangled in the tubing, which can cause injury or even death if the tubing is disconnected and the oxygen flow is interrupted or if the tubing accidentally strangles a patient who is an infant or small child.

Oxygen tents or oxygen hoods are also found in the prior art, and do not suffer the identical disadvantages associated with mask and cannula systems. In a tent or hood type of system, a patient is enclosed in a structure capable of holding in a supply of oxygen. Because the entire environment within the structure is oxygenated, there is no need for tubes or other attachment systems that directly contact the patient. The lack of tubing and attachment systems is an advantage over mask and cannula systems; however, oxygen tents and oxygen hoods are often limited to use in hospital environments, due to the fire and other hazards associated with a structure filled with high concentrations of oxygen. Oxygen tents and hoods also are also disadvantageous because they can suffer from humidity and carbon dioxide buildup, and cannot deliver as precise a mixture of oxygen as a cannula system. Failure to control the levels of oxygen or carbon dioxide around a patient can severely damage a patient's lungs.

SUMMARY

One embodiment of the present invention comprises a plurality of gas delivery ports designed and positioned to result in a therapeutic gas flow being directed towards a resting patient, and the gas delivery ports can be thereby used to deliver oxygen or other forms of respiratory treatment to the patient without any physical contact to the patient.

In a further embodiment of the present invention, one or more gas delivery ports can be controlled individually or in unison, and the volume of flow or orientation of the gas ports can be altered or optimized in response to input or feedback from one or more sensors that detect patient position, patient facial orientation, or other environmental or patient conditions. Such a system can be used to deliver oxygen or other forms of respiratory treatment to a patient without any physical contact to the patient, while at the same time reducing the use and buildup of ambient gases by delivering gases only where necessary.

Another embodiment of the present invention comprises a partial hood designed and positioned to surround a resting patient, in combination with one or more gas delivery ports. The partial hood, or delivery hood, can be used as a mount point for the gas delivery ports and also for various sensors. In addition, the partial hood can allow for a local increase in the concentration of oxygen or other therapeutic gases, but with reduced chances for the detrimental gas and humidity buildup issues associated with a full oxygen tent or hood. The partial hood can be made adjustable, can be made of a breathable material, and thereby be used to control the level of gases surrounding a patient. The partial hood may also be made partially collapsible or otherwise adjustable in size and shape in order to provide access to the patient, to further control the positioning of the gas delivery ports around the patient, to fit or mount around a patient in a variety of applications or environments, or to be made more transportable. The partial hood can provide an isolating or calming effect if the patient is a small child. The partial hood may be decorative to further this effect.

Recent research reveals that many patients, for example children with interstitial lung disease, may benefit from even very low level increases in ambient oxygen. The present invention represents a direct application of this new research, and is a novel approach that is well suited to delivering low levels of oxygen treatment in a home environment for small children and infants. Traditional oxygen therapy has focused on delivering higher levels of oxygen, and has generally utilized systems with patient contact or enclosure to optimally deliver this higher level of oxygen. The present invention is a significant contrast to such methods. It is discovered that low levels of oxygen can be efficiently delivered without requiring direct contact to or full enclosure of a patient. The present invention is an advantage over traditional cannula and mask type systems in that direct attachment of tubing, masks, or ports to the patient is not required. The present invention is an advantage over traditional tent or hood type systems in that it does not require an enclosure; therefore, humidity, carbon dioxide, and oxygen build up problems associated with tent and hood type systems can be substantially reduced.

Even though designed for use in a home environment to provide oxygen for infants and children with interstitial lung disease, embodiments of the present invention are also useful by adults or useful in veterinary care, are fully compatible with traditional oxygen treatment requiring high concentrations of oxygen, and are also readily adaptable for use with other types of respiratory treatment or anesthesiology. Patients include those seeking medical treatment, as well as those for which such a system can provide comfort or other benefit. The term "patient" is not to be restricted to those under a physician's care, but is to be applied to and is inclusive of persons not under a physician's care, including anyone who may make use of an embodiment of a respiratory treatment delivery system of the invention. Further, the term "patient" can include an animal.

BRIEF DESCRIPTION OF THE DRAWINGS

The invention may be more completely understood in consideration of the following detailed description of both the prior art and various embodiments of the invention in connection with the accompanying drawings, in which.

Figure 1:
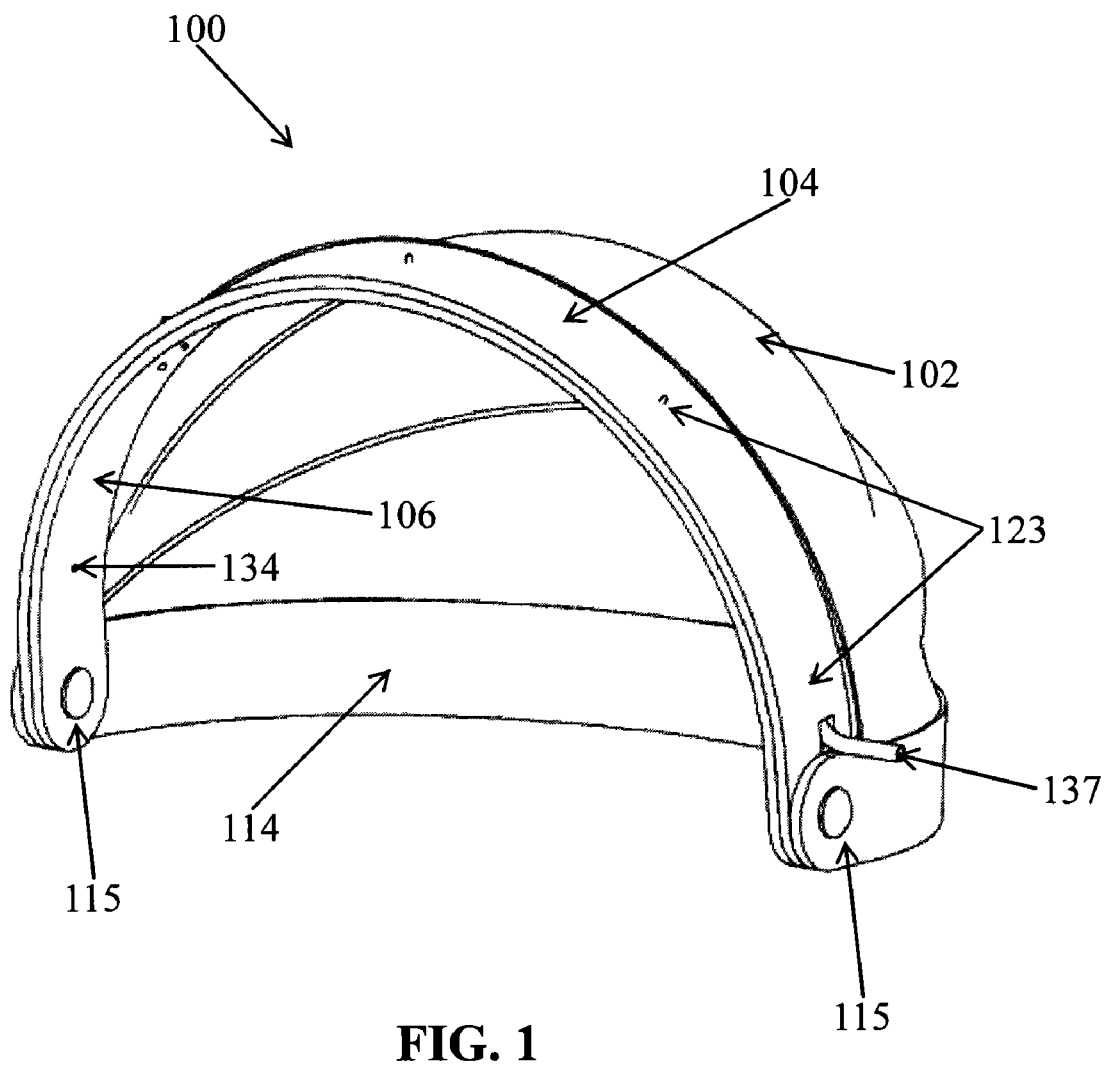
FIG. 1 is a perspective view of a respiratory treatment system according to an embodiment of the invention.

While the invention is amenable to various modifications and alternative forms, specifics thereof are shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the claims.

DETAILED DESCRIPTION

Figure 6:
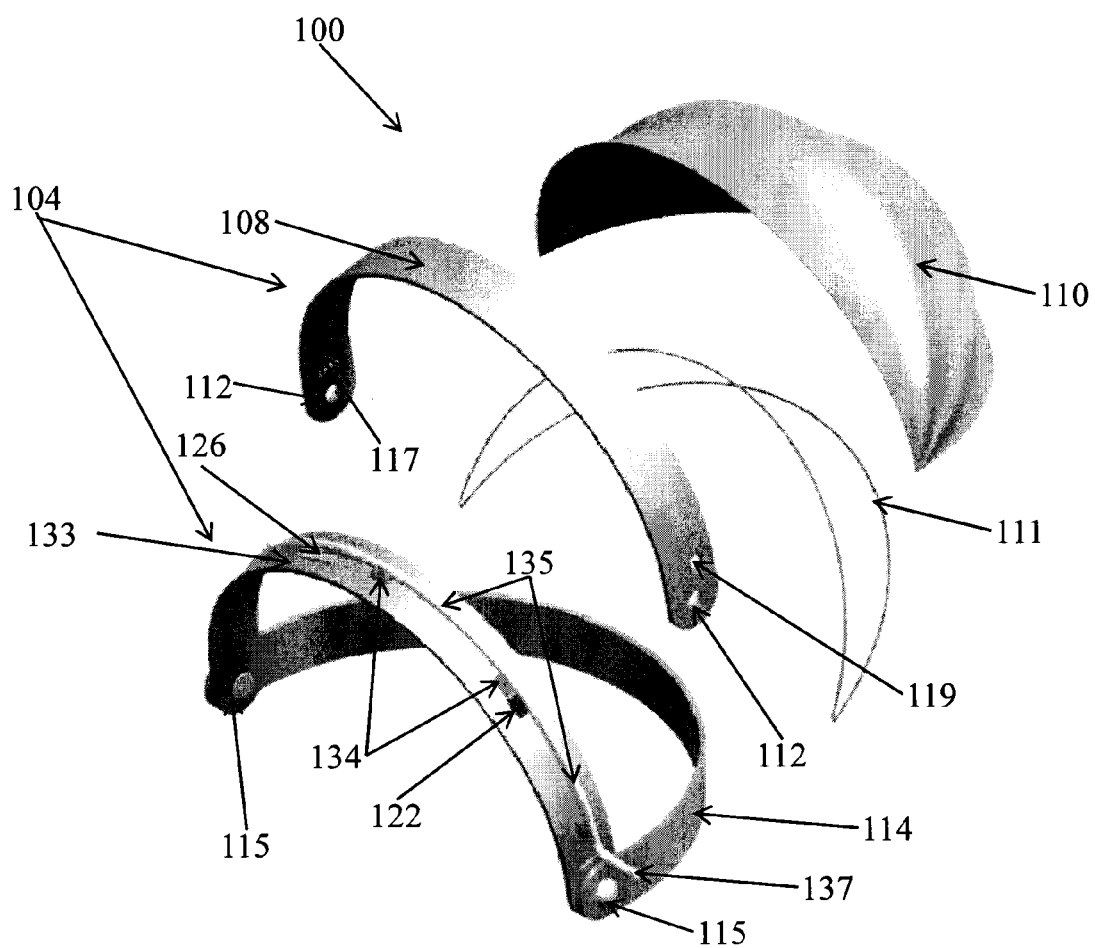
FIG. 6 is an exploded view of a respiratory treatment system according to an embodiment of the invention.

Referring to FIG. 1, there is illustrated one embodiment of a respiratory treatment system 100 according to the present invention. This embodiment comprises three main components: a base support member 114, an optional hood 102, and an integration center 104. The integration center 104 further comprises a gas distribution system 106, with one or more gas inlet ports 137 and one or more gas delivery ports 134. The gas delivery ports 134 disperse oxygen or other therapeutic gases out of the concave side, or inside, of the respiratory treatment system 100. General operation of the respiratory treatment system 100 in FIG. 1 is to provide respiratory treatment to a patient resting under the concave side of the apparatus by delivering therapeutic gases, particularly oxygen from an oxygen source or oxygen concentrator, into the gas inlet ports 137, and then directing that gas towards the patient through the gas distribution system 106 and gas delivery ports 134. The gas flow and direction can be controlled using input or feedback from the sensors 126 mounted within the integration center 104 as shown in FIGS. 6 though 9, or optionally from sensors external to the embodiment shown. Operation of the gas delivery ports 134 or other system elements can be indicated by LEDs or other indicators 123. This embodiment as described allows for the delivery of oxygen or other therapeutic gases to a patient without the necessity of physically contacting the patient, and without placing the patient in a fully enclosed environment. The optional hood 102 in FIG. 1 can be used to both increase gas saturation levels around the patient, as well as dissipate any unwanted or overly concentrated gases or vapors at the same time.

Figure 2:
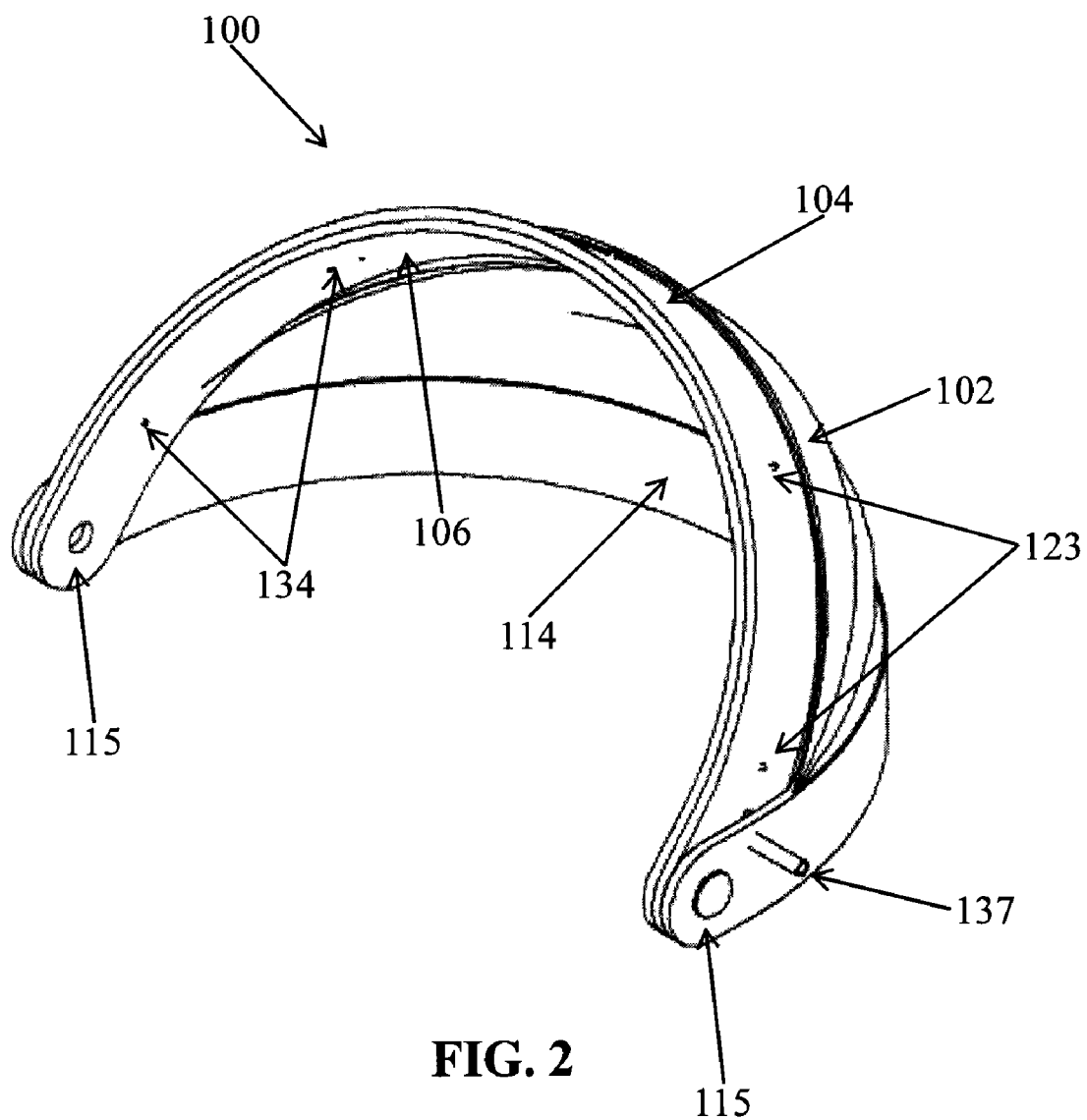
FIG. 2 is a perspective view of a respiratory treatment system with a partially collapsed covering according to an embodiment of the invention.
Figure 3:
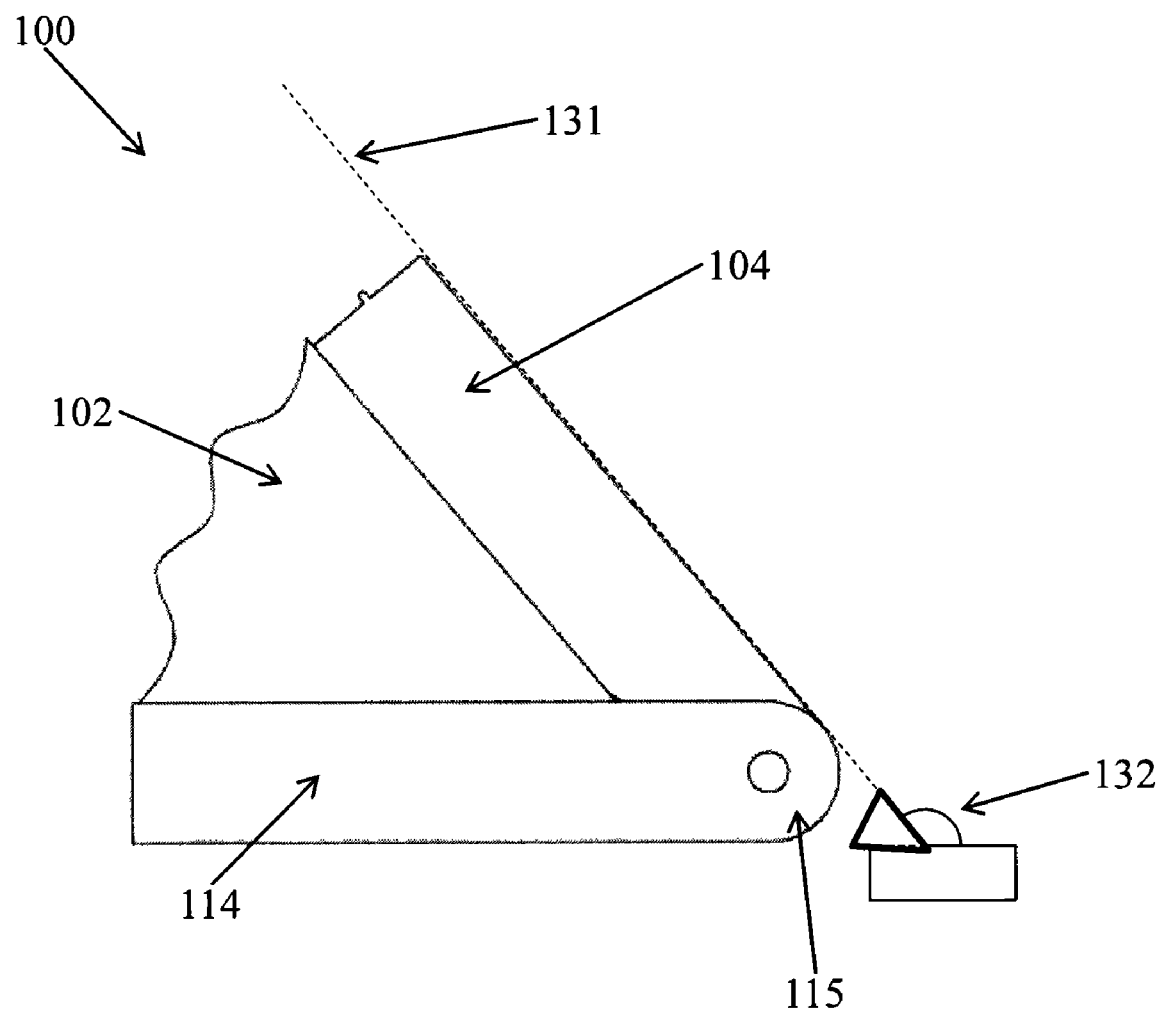
FIG. 3 is a partial left side view of a partially retracted respiratory treatment system according to an embodiment of the invention.

The respiratory treatment system 100 in FIG. 1 can be made adjustable to cover more or less of a resting patient. FIG. 1 shows a pair of joints 115 which connect the base support member 114 to the integration center 104. These joints can be constructed to be moveable, and allow the base support member 114 and integration center 104 to pivot about the joint 115. By pivoting the integration center 104 about a moveable joint 115, the plane 131 can be altered or retracted as shown in FIGS. 2 and 3. The partial enclosure formed as described is characterized by the enclosure formed by the hood 102 as well as other components of the entire respiratory system 100, with an open plane 131 intersecting the structure at an opening angle 132. The opening angle is 180 degrees when the respiratory treatment system 100 is fully open or retracted, 90 degrees when the respiratory treatment system 100 is halfway closed generally as shown in FIGS. 1, and 0 degrees when the respiratory treatment system is fully closed or extended or un-retracted. In the embodiment shown a fully open system at 180 degrees allows for the integration center 104 to be collapsed and nestled inside the base member 114.

Figure 4:
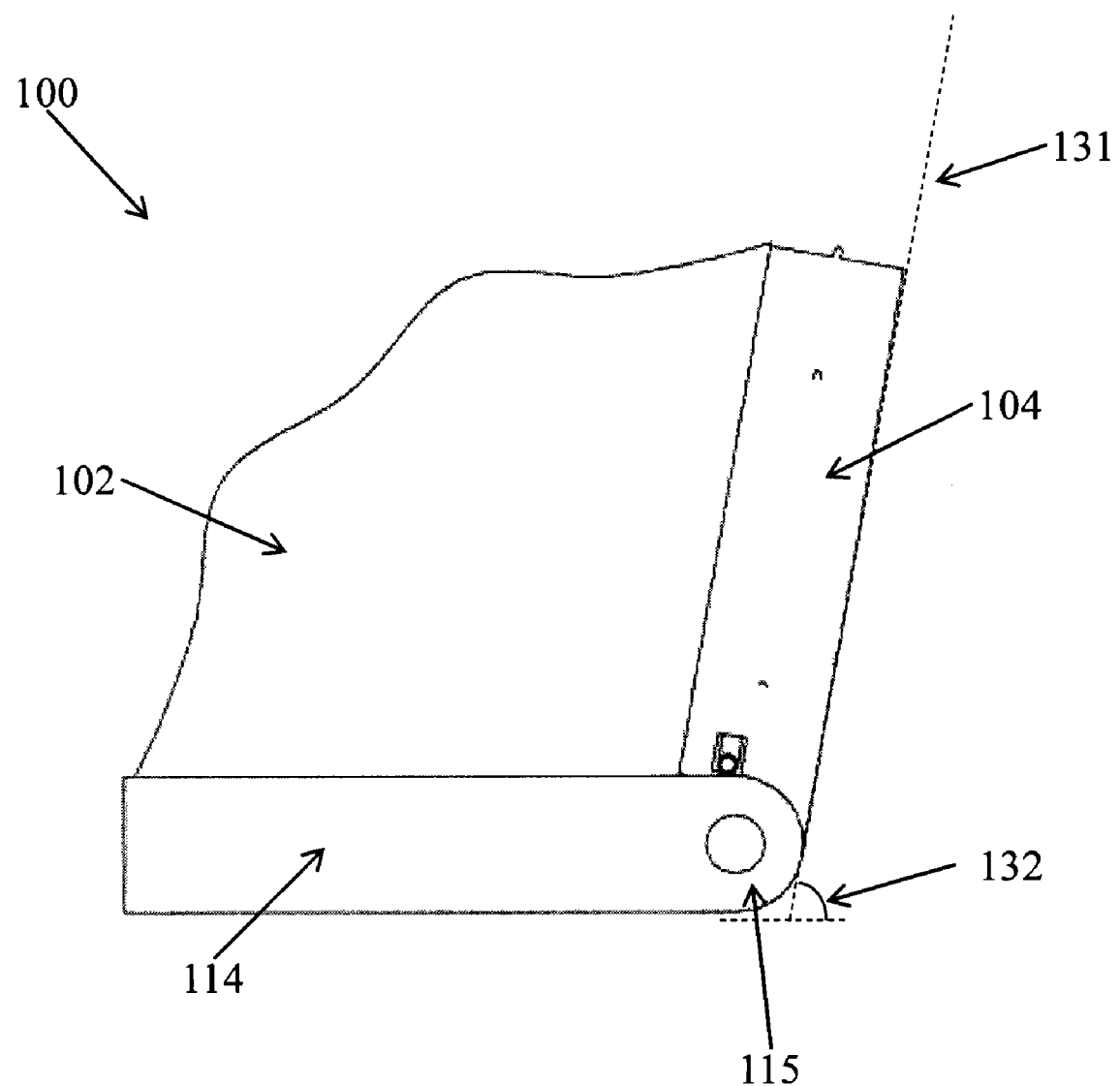
FIG. 4 is a partial left side view of a less partially retracted respiratory treatment system according to an embodiment of the invention.

The pivoting movement about the joints 115 as shown in FIGS. 2 and 3 can be used in a more retracted or open position to either provide access to the patient, or to reduce the level of gas buildup surrounding the patient, or optimally position any gas delivery ports 134 or sensors located in the integration center 104 or hood 102 above the patient. Alternatively, FIG. 4 is a partial side view of the respiratory treatment system 100 shown in FIG. 1 in a more closed or more un-retracted position. By pivoting the integration center 104 about a moveable joint 115 as shown, the plane 131 can be altered to cover more of the patient. This larger coverage can be used to isolate the patient, increase the local level of oxygen or other therapeutic gases around the patient, or optimally position any sensors or gas delivery ports 134 contained within the integration center 104 or hood 102 above the patient.

Figure 5:
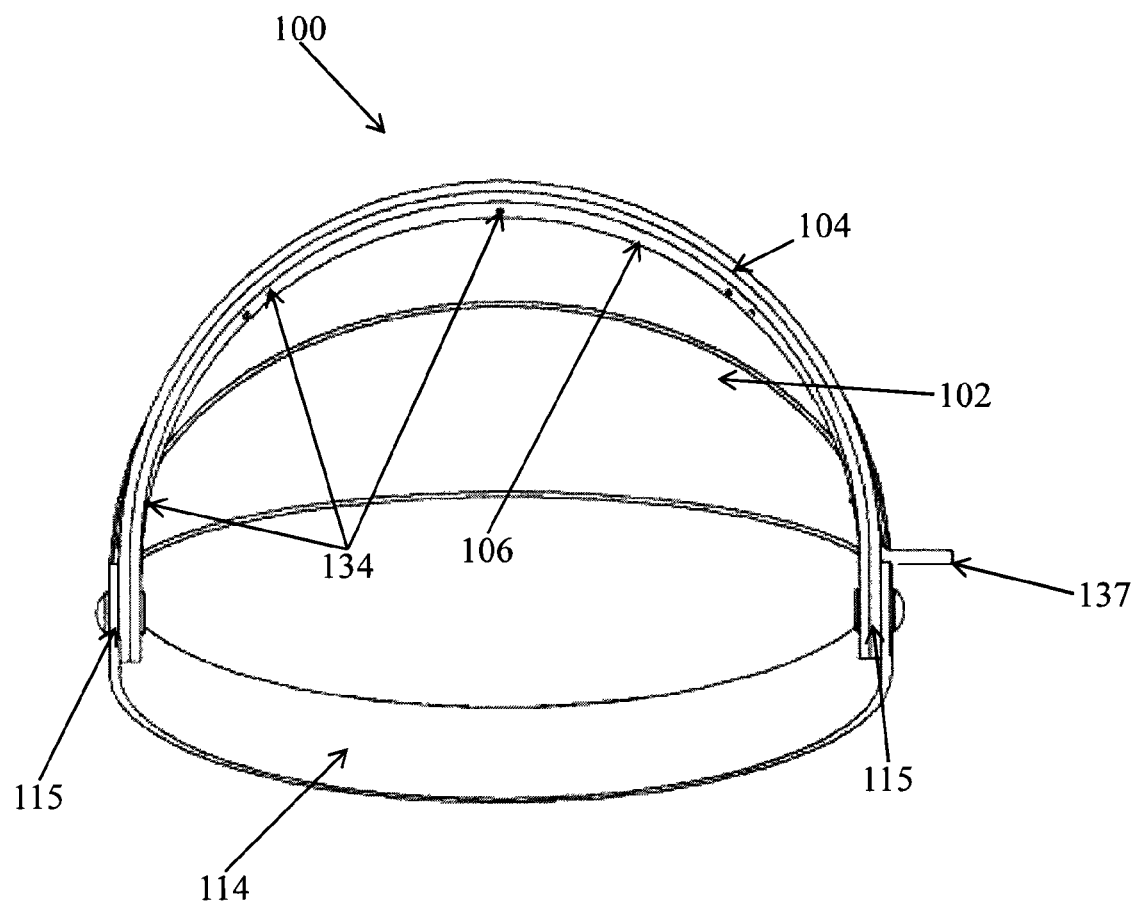
FIG. 5 is a front perspective view of a respiratory treatment system according to an embodiment of the invention.
Figure 9:
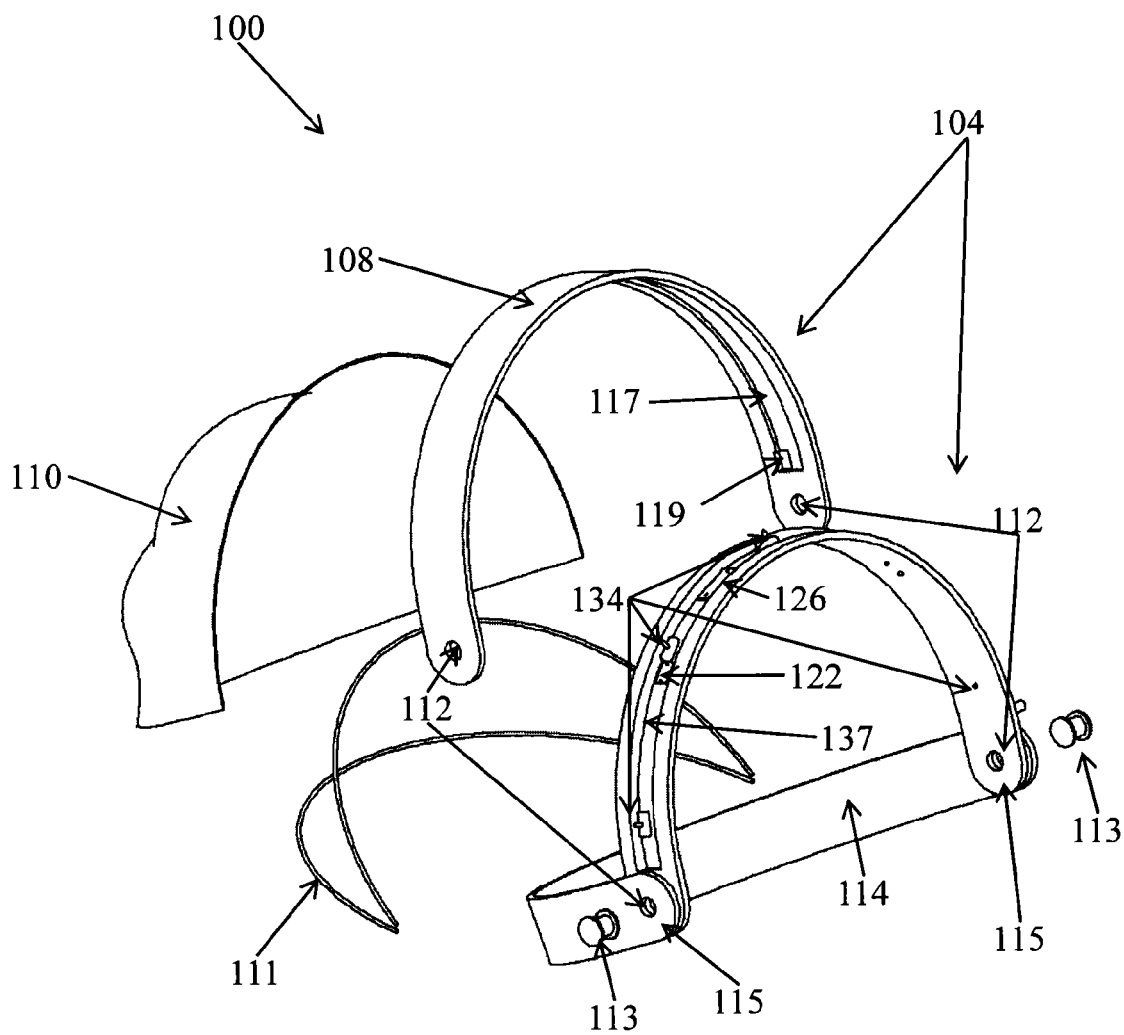
FIG. 9 is an exploded view of a respiratory treatment system according to an embodiment of the invention.

The joints 115 from FIG. 1 are also shown in FIGS. 5 and 9, which are a front perspective view and a side perspective view, respectively, of the embodiment illustrated in FIG. 1. In FIG. 9, the joints 115 are shown with a single joint fastener 113 passing through each joint aperture 112 thereby connecting the base support member 114 to the integration center 104, the integration center 104 generally comprising a distribution manifold 133 and a top structural member 108. If a single joint fastener 113 is utilized in each joint 115, then the joint 115 can be readily made movable, with the base support member 114 and integration center 104 pivoting about the joint using the fastener as an axle to support the movement. Not shown in FIG. 9, the joints 115 could also comprise a fastener free detent and indentation type of joint, or comprise another form of hinge instead of a fastener, or any number of means known in the art for making pivoting or hinged joints, and still perform the same pivoting function. The pivoting mechanism can be enhanced by adding a means of holding the plane 131 stable after adjustment. For example, some friction, ratcheting mechanism, or series of bumps and detents can be added in between the surfaces where base support member 114 and the integration center 104 come in contact with one another. Many other means are known in the art for arresting the movement of such a joint; for example pistons, tie downs, stop blocks. These can otherwise be added or utilized in the joint 115.

In the alternative, the joint 115 of FIG. 1 can be made rigid by using a single or multiple fasteners, or a series of detents, or a tongue and groove or other fittings known in the art, or could be made from a single continuous piece of material partially or wholly forming both the base support member 114 and the integration center 104. In the case where the joints 115 are not moveable or the hood 102 is not flexible, one embodiment would comprise a system where sensors or gas delivery ports 134 would be stationary, while still other embodiments could comprise a system where the sensors or gas delivery ports 134 could be moveable, adjustable to point in a different direction depending on the location of a patient, or located elsewhere around the patient.

FIGS. 6, 7, 8a, and 9 are exploded views of the respiratory treatment system 100 depicted in FIG. 1. As again shown in these Figures, a base support member 114 is connected to an integration center 104 by the pair of joints 115. An optional hood 102 can be positioned in between or integrated with the base support member 114 and integration center 104 to create a partially enclosed space on the concave side of the respiratory treatment system 100. This enclosed space can then be positioned over a patient. In some embodiments, a hood is not necessary if the gas delivery ports 134 are designed to provide sufficient gas delivery to reach a patient's nose and mouth without the need for a hood to assist in increasing the level of gas concentration. In embodiments where a hood is utilized, the hood 102 can be made from a covering member 110 comprising a material such as cloth, plastic, or other preferably flexible material; and an optional support member 111. If the hood material in covering member 110 is flexible, it will allow for the expansion or reduction of the enclosed space as the integration center 104 is pivoted about the joint 115, if the joint 115 is constructed to be moveable. To help control the gas concentration under the hood 102, a flexible covering member 110 may be made of either a gas impermeable material, for example, plastic or vinyl film, to help hold gases near a patient, or be made of a gas permeable membrane or fabric, for example, cotton, linen or nylon, to help disperse gases under the hood.

The covering member 110 can be clear or transparent to allow visibility, or the covering member 110 may also be opaque or partially opaque to provide a potentially isolating and calming effect to the patient, or the covering member may be a combination thereof. The covering member may also be decorative in its printed design or in its shape to help provide a calming effect on the patient, especially a small child. As an example, for children, a toy-like or animal shape or print may be appropriate. There are many alternative constructions for the covering member 110 and support member 111 that will be readily apparent to one skilled in the art. The hood is designed to allow for sufficient saturation of oxygen or other therapeutic gases when required by the application or particular usage, and also allow for dissipation of gases or vapors when required by the application or particular usage.

The covering member 110 can also comprise a partially or completely rigid shell, in which case a suitable material for the rigid portion would include a hard plastic or similar material. For a rigid shell, the covering member 110 can be made permeable by adding vents or vent holes into the shell, or be constructed with a partially permeable material, or be made part flexible and part rigid, with the flexible portion adjustable to control the buildup of gases.

For flexible covering members 110, the support member 111 is preferably constructed of a flexible metallic wire or plastic. Alternatively, the support member 111 can comprise a series of rigid supports approximating the shape of the base support member 114 or integration center 104, so as to facilitate folding or retraction of the hood 102 while maintaining a consistent shape to the overall respiratory treatment system 100. In addition, the support member 111 can be constructed to help define a decorative shape to the hood 102. Further, the support member 111 may be adapted to serve as a mount point for additional sensors 126 or gas delivery ports 134.

FIG. 9 shows an embodiment with a base support member 114, a pair of joint apertures 112, and a pair of joint fasteners 113 which can be used to connect the base support member 114 to the integration center 104. In the embodiment shown in FIG. 9, the base support member 114 comprises an arc, although other shapes, for example, rectangular, circular, oval, or yet other shapes are contemplated. Also in the embodiment shown, the integration center 104 is designed to be the same general shape as the base member 114, whereby if used in conjunction with a moveable joint 115, the base support member 114 and integration center 104 can be folded together for easy transport or storage. In other embodiments, the integration center 104 would not have to be a similar shape as the base support member 114, however in some cases this could impede the ability of the apparatus to fold compactly.

In other embodiments, the base support member 114 further comprises a set of clamps or ties that allow the base member to be attached to a crib, bed, or other structure. In still other embodiments, the base support member 114 further comprises legs that can extend to a floor, table, or other supportive structure, thereby allowing the apparatus to be positioned over, for example, a crib or bed. The legs, or the legs connection to the base member, can be constructed to further allow the base support member 114 to be raised and lowered over a patient using, for example, a plug and hole type of system, a ratchet type system, or a friction type adjustment system. In still other embodiments not shown, the base support member 114 can further comprise clamps or slots to allow attachment of the respiratory treatment system 100 to a wall, headboard, or other planar surface. In still other embodiments not shown, the base support member 114 can be mounted so as to swivel around or over a patient in order to allow easier access to the patient, or in order to optimally position the entire respiratory treatment system 100 over the patient.

Figure 7:
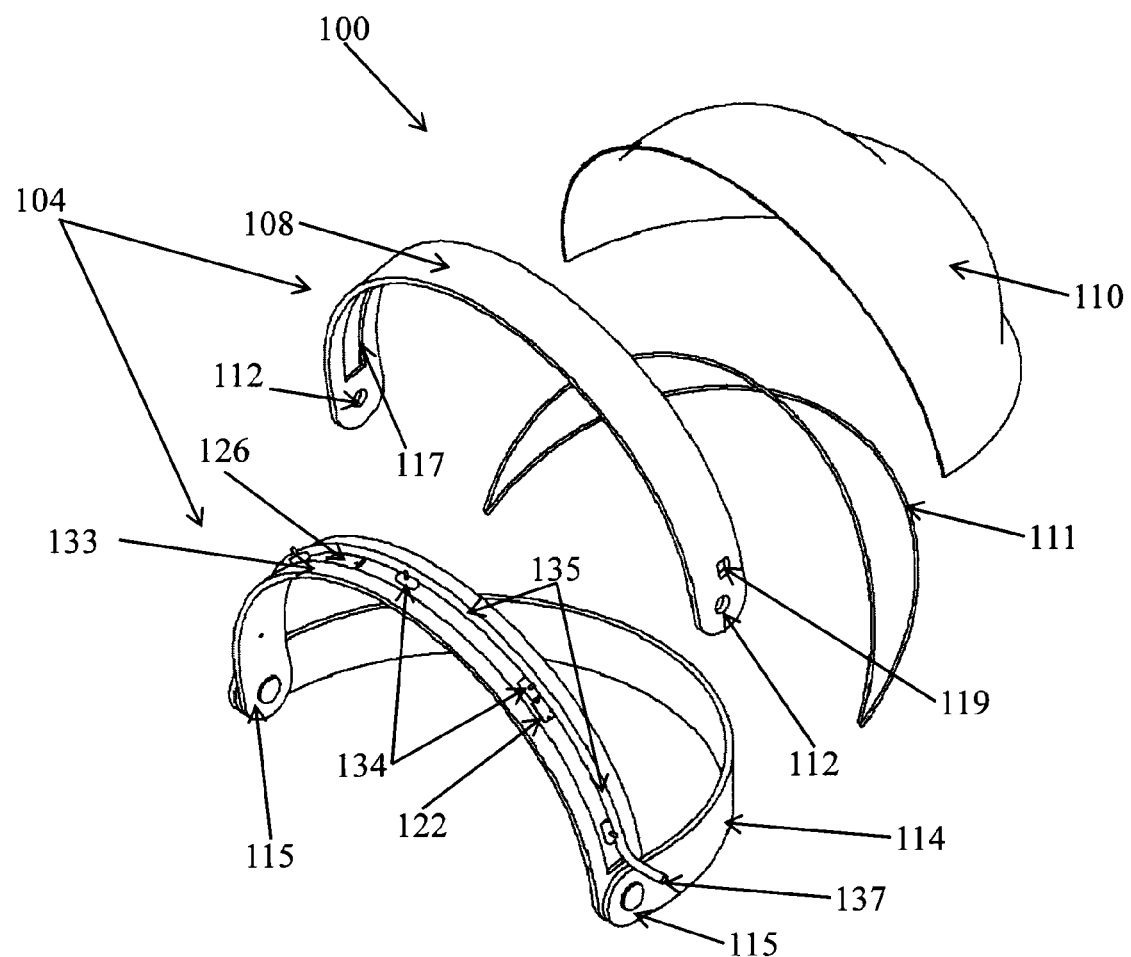
FIG. 7 is an exploded view of a respiratory treatment system according to an embodiment of the invention.
Figure 8B:
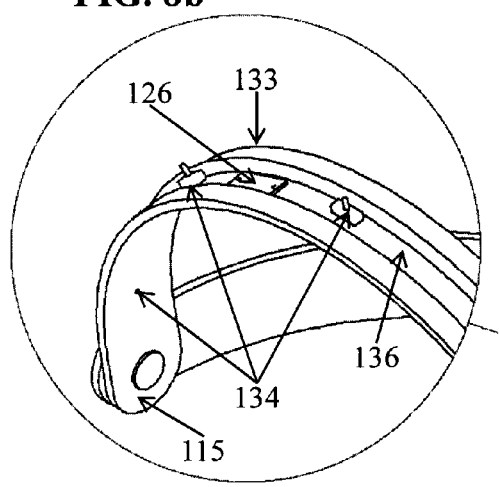
FIG. 8b is a detailed perspective view of the integration center of a respiratory treatment system shown in FIG. 8a according to an embodiment of the invention.
Figure 8A:
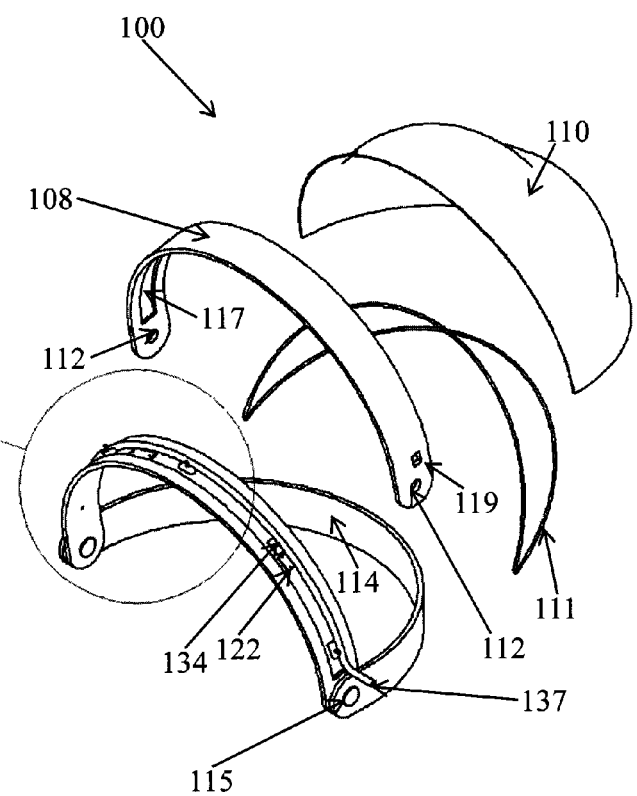
FIG. 8a is an exploded view of a respiratory treatment system according to an embodiment of the invention.

The integration center 104 as depicted in the embodiment shown in FIG. 1 is also further illustrated by the exploded views of FIGS. 6, 7, 8*a*, and 9. In the illustrated embodiment, the integration center 104 includes a distribution manifold 133, housing one or more gas delivery ports 134. The gas delivery ports 134 can be mounted on the distribution manifold 133 in an optional recessed distribution channel 136, and pass gases from the convex (top) to the concave (bottom) side of the distribution manifold 133 as shown in detailed FIG. 8*b*. The gas delivery ports 134 can be operated in unison, or individually controlled. One or more control units 122 as shown in FIGS. 8*a* and 9, which control the operation of one or more of the gas delivery ports 134, can also be mounted within the integration center 104. In some cases, a gas delivery port and control unit will comprise a single integrated unit. The control units 122 can comprise a transducer or valve that controls gas delivery in response to an external electrical, pneumatic, hydraulic, or other signal; or in addition the control units 122 can further comprise an electronic control unit, for example, a microcontroller that directly controls the gas delivery by use of an internal signal. Gas delivery can be controlled by a preset algorithm, or it can be controlled in response to one or more sensors 126. Integrated sensors 126 can be mounted directly to the integration center 104, or can be mounted elsewhere including around or underneath a patient, in direct connection with a patient, or inside the optional hood 102 or base support member 114. The sensors 126 can send information directly to a controller 122 or to a gas delivery port 134. In addition, the sensors 126 can send information to an external control or monitor device, for example, an electronic computer, alarm, or LCD display. Many sensor types can be effectively utilized in this kind of system, including gas sensors, thermal sensors, acoustic sensors, pulse oximeters, visible spectrum cameras, infra-red cameras, sonar frequency sensors, color-to-frequency sensors, pressure and moisture sensors, blood monitoring systems, or any sensor that suitably detects environmental or patient conditions.

As shown in FIG. 7, a gas distribution tubing 135, comprising one or more tubes, can be used to route oxygen or other therapeutic gases from one or more gas inlet ports 137 to the gas delivery ports 134. The optional recessed distribution channel 136 as shown in FIG. 8*b* can also be structured to distribute gases to the gas delivery ports 134 without the necessity of delivery tubing 135. The gas inlet ports 137 can be mounted in any position along the integration center and can operatively attach to one or more tubes or channels to facilitate gas distribution.

A top structural member 108 shown in FIGS. 6, 7, 8*a*, and 9 can be used to protect and enclose the components of the integration center 104 via mounting on top of the gas distribution manifold 133. An optional recessed band 117 allows room for the top structural member 108 to mount onto the distribution manifold 133, and also optionally carry therapeutic gases within the cavity formed between the top structural member 108 and the distribution manifold 133 by the recessed band 117 or recessed distribution channel 136. Apertures 119 can be added to the top structural member 108 in order to allow access to any gas inlet ports 137, and joint apertures 112 can be added where required to allow a fastener to pass through the joint 115.

While the integration center 104 in the embodiments shown in FIGS. 1 through 9 has a generally concave band-like shape, the particular embodiments shown are not intended to be limiting. Such an integration center 104 could comprise any number of cross sectional shapes, including rectangular, circular, or other shape suitable for positioning one or more gas delivery ports and optionally one or more sensors above a patient. The integration center 104 does not require a top structural member 108, and the sensors 126 and gas ports 134 can be mounted on either the concave or convex side of the distribution manifold 133. In addition, the integration center 104 and overall shape of the respiratory system 100 as shown is nominally a quarter sphere or arc. However, any number of overall shapes are suitable, including rectangular, conical, or even decorative shapes. The sensors 126 and gas distribution ports 134 are not required to be mounted within any integration center. In some embodiments, gas distribution ports 134 or sensors 126 may be mounted within the hood 102 or within the base support member 114, or elsewhere around a potential patient, and an explicit structure for the integration center 104 may not be necessary or the integration center may serve as solely as a top member providing structural support. The integration center is also not limited to an arc or other shape in a single plane, but may also incorporate other curves, branches, or appendages in any direction to enable optimization of the location of the gas distribution ports 134 and sensors 126 around a particular type of patient, or to better serve in a particular type of application. To this end, a shape is provided consistent with enabling the adequate capture of oxygen or other gases in systems where a hood 102 is required for such a purpose, and to provide for suitable proximity of the gas ports to the patient when required.

Figure 11A:
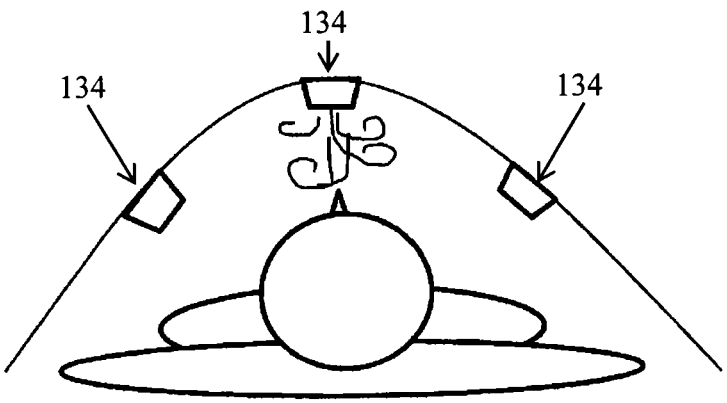
FIG. 11a is a back sectional view of a respiratory treatment system with a patient facing upward according to an embodiment of the invention.
Figure 11B:
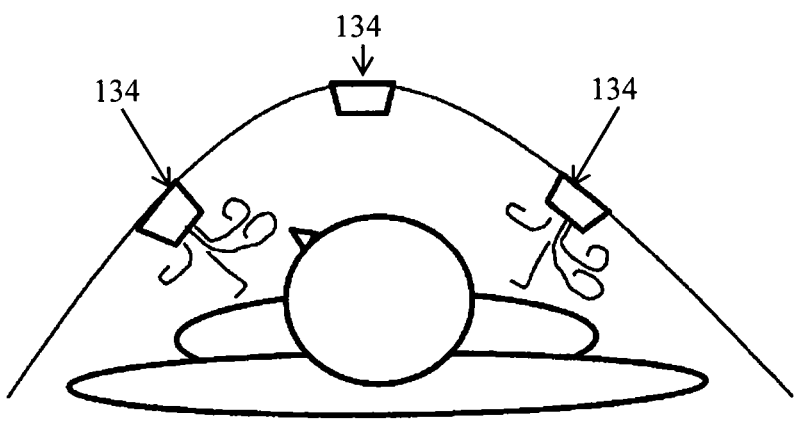
FIG. 11b is a back sectional view of a respiratory treatment system with a patient facing leftward according to an embodiment of the invention.
Figure 11C:
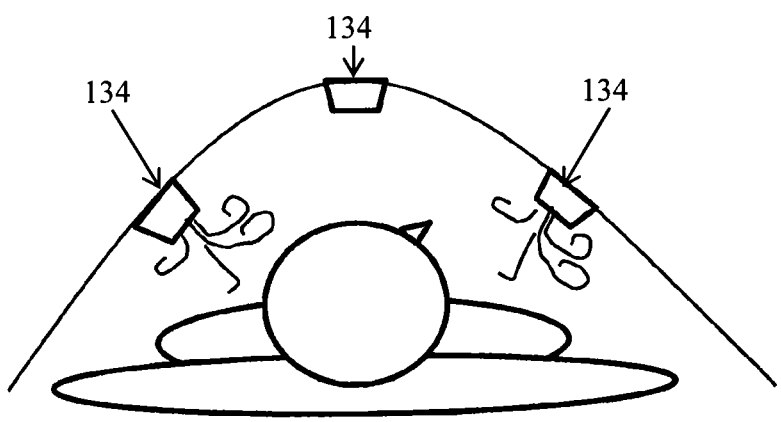
FIG. 11c is a back sectional view of a respiratory treatment system with a patient facing rightward according to an embodiment of the invention.

The detailed operation of one embodiment of the invention similar in structure to the embodiments shown in FIGS. 1 through 9 is shown in back cross sections in FIGS. 11*a*, 11*b*, and 11*c*. The embodiment of FIGS. 11*a*-11*c*, which can be used with or without a partial hood, delivers therapeutic gases to a patient by favorably diverting gas flow to one or more gas distribution ports 134. FIG. 11*a* shows a cross section of a patient lying down and facing directly upwards. In FIG. 11*a*, a positional or other sensor is used to deduce the direction of the patient's face and the system favorably diverts gas flow to a centrally located gas delivery port or ports 134 above or directed towards the patient's upwardly facing nose and mouth. In FIG. 11*b* and 11*c*, a similar cross section shows gas favorably diverted to gas delivery ports 134 located to or directed at the patient's left and right when the system deduces that the patient is no longer facing directly upward.

In one embodiment not shown directly by FIGS. 11*a*-11*c*, a system of three gas delivery ports 134 with placement similar to FIGS. 11*a*-11*c* is described. If a patient's head is detected as facing or positioned straight up, only the centermost gas delivery port is turned on or enabled, with both remaining side gas delivery ports remaining closed or restricted. If a patient's head is later detected as facing or positioned to the left, the center and rightmost gas delivery ports will be closed or restricted, and the leftmost gas delivery port will be opened or enabled. Similarly, if the patient's head is detected as facing or positioned to the right, the center and leftmost gas delivery ports will be closed or restricted, and the rightmost gas delivery port will be opened or enabled. If the patient's head is detected as facing or positioned, for example, forty-five degrees left, both the center and leftmost gas delivery ports will be opened or enabled, while the rightmost gas delivery port will be closed or restricted. Likewise, if a patient's head is later detected as facing or positioned forty-five degrees right, both the center and rightmost gas delivery ports will be opened or enabled, while the leftmost gas delivery port will be closed or restricted.

In another embodiment not shown directly by FIGS. 11a-11c, a system with five gas delivery ports 134 is described, wherein the leftmost, top, and rightmost gas delivery ports are similarly positioned as the gas delivery ports 134 in FIGS. 11a-11c; and a left intermediate gas delivery port is added and placed between the center and leftmost gas delivery ports 134 of FIGS. 11a, 11b, and 11c; and a right intermediate gas delivery port is added and placed between the center and rightmost gas delivery ports 134 of FIGS. 11a, 11b, and 11c. The gas delivery ports in the described arrangement may be opened or enabled in groups of one or more while the others are closed or restricted in response to detection of a patient's facial position. For example, in one embodiment, if a patient's head is detected as facing or positioned straight up, the center, left intermediate, and right intermediate gas delivery ports are opened or enabled, while the leftmost and rightmost gas delivery ports are closed or restricted, thereby directing oxygen most efficiently toward the upward facing patient. If the patient's head is later detected as facing or positioned to the left, the center, left intermediate, and leftmost gas delivery ports are opened or enabled, while the right intermediate and rightmost gas delivery ports are closed or restricted, thereby directing oxygen most efficiently toward the leftward facing patient. Similarly, if the patient's head is detected as facing or positioned to the right, the center, right intermediate, and rightmost gas delivery ports are opened or enabled, while the left intermediate and leftmost gas delivery ports are closed or restricted, thereby directing oxygen most efficiently toward the rightward facing patient.

In another embodiment not shown directly by FIGS. 11a-11c, if a patient's head is detected as facing or positioned straight up, the center gas delivery port is opened or enabled, while all other gas ports are closed or restricted, thereby directing oxygen efficiently toward the patient. If the patient's head is later detected as facing or positioned approximately 45 degrees to the left, the left intermediate gas delivery port is opened or enabled, while all other ports are closed or restricted, thereby directing oxygen efficiently toward the patient. If the patient's head is later detected as facing or positioned approximately 90 degrees to the left, the leftmost gas delivery port is opened or enabled, while all other ports are closed or restricted, thereby directing oxygen efficiently toward the patient. In this embodiment, the function of the system to a right facing patient would be symmetric to its function in response to a left facing patient.

In another embodiment not shown directly by FIGS. 11a-11c, if a patient's head is detected as facing or positioned straight up, the center gas delivery port is opened or enabled, while all other gas ports are closed or restricted, thereby directing oxygen efficiently toward the patient. If the patient's head is later detected as facing or positioned approximately zero to forty-five degrees to the left, the center and left intermediate gas delivery ports are opened or enabled, while all other ports are closed or restricted, thereby directing oxygen efficiently toward the patient. If the patient's head is later detected as facing or positioned approximately forty-five to ninety degrees to the left, the leftmost and left intermediate gas delivery ports are opened or enabled, while all other ports are closed or restricted, thereby directing oxygen efficiently toward the patient. In this embodiment, the function of the system to a right facing patient would be symmetric to its function in response to a left facing patient.

The absolute location of a patient's head can also be used, in addition to the direction the patient is facing, to determine which gas delivery ports should be opened. In another embodiment not shown directly by FIGS. 11a-11c, if a patient's head is detected as positioned in the center of a system, the center gas delivery port is opened or enabled, while all other gas ports are closed or restricted, thereby directing oxygen efficiently toward the patient. If the patient's head is later detected as in between the center and left intermediate gas delivery ports, the center and left intermediate gas delivery ports are opened or enabled, while all other ports are closed or restricted, thereby directing oxygen efficiently toward the patient. If the patient's head is later detected as being positioned in between the leftmost and left intermediate gas delivery ports, then the leftmost and left intermediate gas delivery ports are opened or enabled, while all other ports are closed or restricted, thereby directing oxygen efficiently toward the patient. In this embodiment, the function of the system to a right facing patient would be symmetric to its function in response to a left facing patient.

The embodiments described here are for illustration only and in no way limit the degree of angle or patient head placement or method of face detection or head detection, or number of gas delivery ports within a system or sequence of gas delivery port openings. The system is infinitely scalable in the degree to which head detection can be measured, in the quantity and placement of gas delivery ports, and in the progression in which the gas delivery ports can be opened or closed or enabled or restricted. Moveable or directable gas distribution ports could also be utilized to perform the same function as the gas delivery ports 134 shown in FIGS. 11a, 11b, and 11c, wherein the angle or direction in which the gas distribution port directs gas flow can be altered depending on the position or orientation of the patient. The gas delivery ports 134 can direct gas flow towards a patient by either directing a stream of gas at the patient, or by releasing a diffuse distribution of gas from gas ports that are favorably positioned relative to the patient's position or orientation. The gas delivery ports 134 are also not required to be mounted in a single two dimensional cross section as shown in FIGS. 11a, 11b, and 11c. Instead, in some embodiments a three dimensional array of gas distribution ports, or a moveable two dimensional array of ports can be used to deliver therapeutic gases in the event that a patient's entire head changes position during rest. Projecting oxygen or other therapeutic gases in the embodiments described is efficient and effective. It conserves oxygen or other therapeutic gases or vapors by closing or restricting unneeded gas delivery ports and, at the same time, allows oxygen or other therapeutic gases to be precisely and intimately distributed via the opening of gas delivery ports closest to the patient.

Figure 10A:
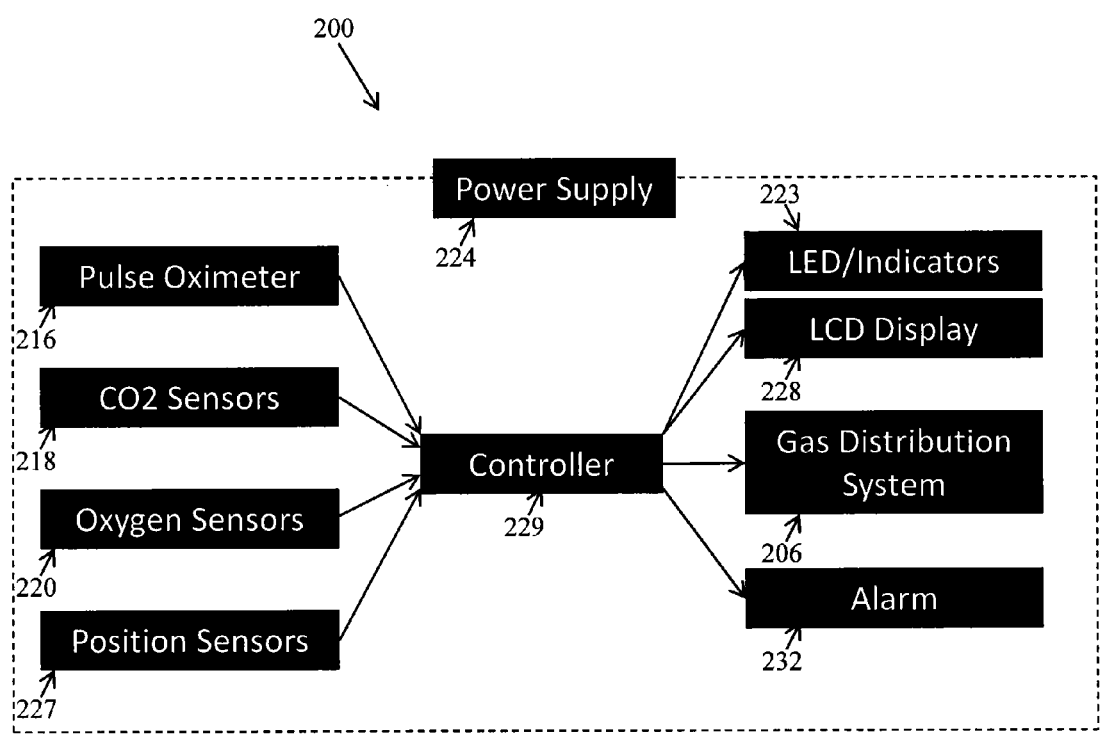
FIG. 10a is a block diagram of sensor and integration components of a respiratory treatment system utilizing one or more sensors according to an embodiment of the invention.
Figure 10B:
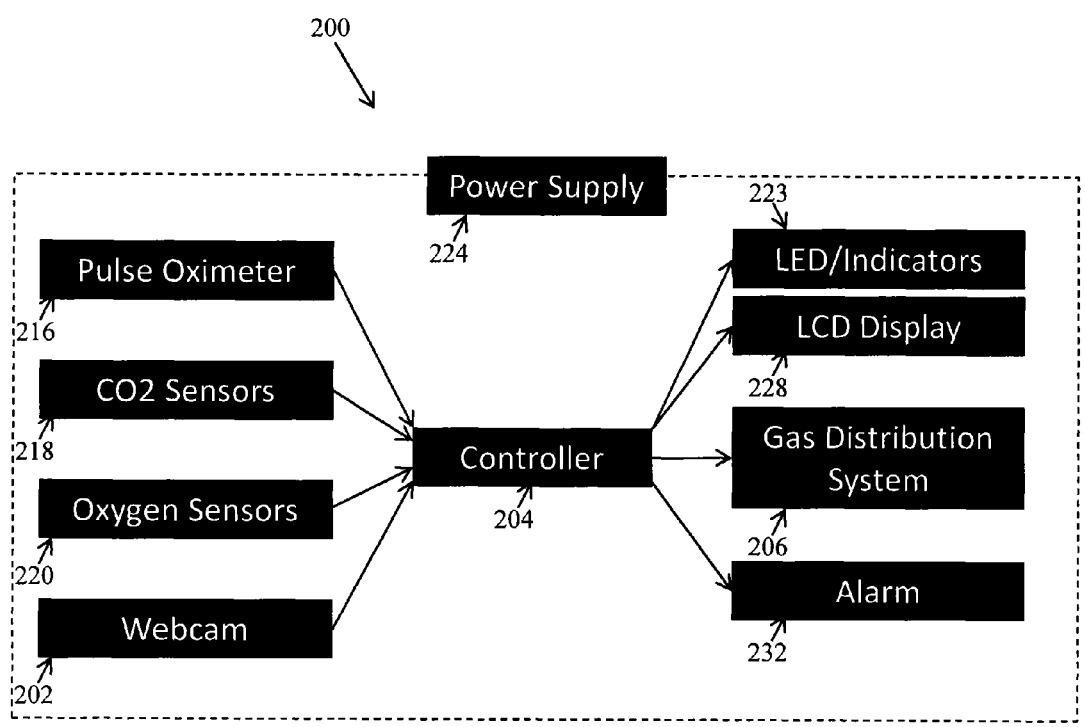
FIG. 10b is a block diagram of sensor and integration components of a respiratory treatment system utilizing a webcam according to an embodiment of the invention.
Figure 10C:
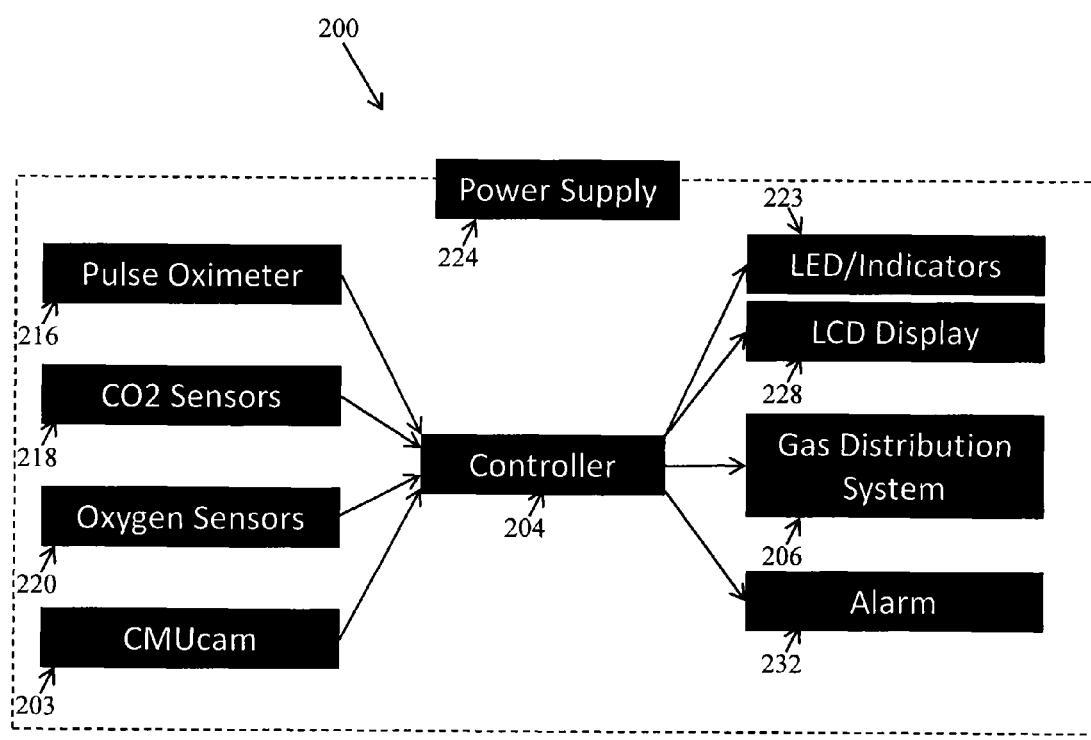
FIG. 10c is a block diagram of sensor and integration components of a respiratory treatment system utilizing a CMUcam according to an embodiment of the invention.

FIGS. 10a-10c are block diagrams that further describe potential embodiments of the invention. FIG. 10a depicts the most general purpose sensor and other components which may be included in some embodiments. Referring to the individual elements shown in the block diagram of FIG. 10*a*, system components generally comprise carbon dioxide sensor or sensors 218 to measure the amount of carbon dioxide surrounding a patient; oxygen or other gas sensor or sensors 220 to measure the amount of oxygen or other therapeutic gases surrounding the patient; position or position sensors 227 to measure the position, orientation, or direction of the patient; power supply or supplies 224 to provide power to various components; controller or controllers 229 to process inputs and provide outputs to the system; LCD or other suitable displays 228 to provide status or updates to the user including current oxygen saturation, carbon dioxide, and other readings; one or more LEDs or other indicators 223 to show function of gas delivery ports and other components; alarm 232 for providing warning in case of a failure or dangerous state; and a gas distribution system 206. Optionally, sensor and integration components may contain a pulse oximeter 216 to measure oxygen saturation in the patient. According to some embodiments, pulse oximeter 216 may be incorporated into a closed-loop control system to control the function of the entire system including ambient oxygen or other therapeutic gas concentrations delivered or surrounding a patient.

More specifically, the controller or controllers 229 in FIG. 10*a* may include microcomputers or personal computers, microcontrollers, or other dedicated electronic circuitry suited to measure, respond, or control a system as shown in the block diagram of FIG. 10*a*. The position sensors 227 in FIG. 10*a* can include pressure sensors mounted underneath a patient, oxygen or carbon dioxide sensors, thermal or infrared sensors, sonar or acoustic sensors, webcams, video cameras, digital cameras, color to frequency detectors, or any other means of detecting the position or facial direction of a patient. Position sensors can also include a CMUcam, a low-cost computer vision device originally made by Carnegie Mellon University. Suitable displays 228 include LCD, LED, CRT, dot matrix, or other electronic means of displaying alphanumeric characters, or graphical indicators. The LCD or other suitable display 228 can be used to show current oxygen prevalence, oxygen saturation of the patient, current carbon dioxide measurements, and any other useful measurements taken by various sensors. The LCD or other suitable display 228 may also be utilized for a user interface to provide controls of the system by integrating a touchscreen, buttons, keypad, keyboard, or the like. In conjunction with a display or displays, LEDs, light bulbs, or other similar indicators may be used to indicate the state of various sensors or other system components. The gas distribution system 206 may comprise an oxygen source or oxygen concentrator, other therapeutic gas sources, a humidity control system, a temperature control system, tubing or channels or other mechanisms for distributing gases, and one or more nozzles, ports, diffusers, or other mechanisms for delivering gas flow to a patient.

As depicted by FIG. 10*a*, in some embodiments the pulse oximeter 216, carbon dioxide sensors 218, oxygen or gas sensors 220, and position sensors 227 provide inputs or feedback to one or more controllers 229. The controller or controllers 229 may use the inputs or feedback to appropriately output information to one or more LCD or other suitable displays 228, to control LEDs 223, to control gas flow or direction in the gas distribution system 206, and also trigger any alarm 232. When using electrical power, such a system may benefit from utilizing a battery backup. The objective of the embodiment shown in the block diagram of FIG. 10*a* is to efficiently and safely control oxygen or other respiratory treatment to a patient.

FIG. 10*b* shows a particularized variation of FIG. 10*a*, wherein a webcam 202 is used in conjunction with controller 204 to measure the position or orientation of the patient, control various LCD or other suitable displays 228, control the gas distribution system 206, and trigger any alarm 232. FIG. 10*c* shows another particularized variation of FIG. 10*a*, wherein a CMUcam 203, a low-cost computer vision device originally made by Carnegie Mellon University, is used to measure the position or orientation of the patient, control various LCD or other suitable displays 228, control the gas distribution system 206, and trigger any alarm 232. In the block diagrams 10*a*-10*c*, one particular way that a camera can be used is to detect the position, angle, direction, or orientation of the eyes, nose, or mouth. Based on this information, the system can be directed to deliver respiratory treatment to the patient as depicted in FIGS. 11*a*-11*c*. In addition, the camera can be used to detect the movement of the patient from underneath the system or detect the movement of the patient into an otherwise unsafe position or condition, and send a signal to an alarm 232.

In yet another embodiment not shown specifically in FIG. 10*a*, a pressure sensitive pad is placed in a position known to the system in relation to the oxygen distribution system. Pressure applied by the patient's body activates sensors inside the pad, and the sensors provide input to a controller or controllers 229 in a system as shown in FIG. 10*a*. For example, the pressure sensitive pad can be used to detect the position of a patient. Based on this information, the system can be directed to deliver respiratory treatment to the patient as depicted in FIGS. 11*a*-11*c*. In addition, the pressure sensitive pad can be used to detect the movement of the patient from underneath the system or detect the movement of the patient into an otherwise unsafe position or condition, and send a signal to an alarm 232.

Thus, referring to FIGS. 10*a*, 10*b*, and 10*c* generally, position sensors 227, webcam 202, or CMUcam 203, process sensory inputs using thermal, visual, pressure, proximity, or other means, to detect the position, orientation, direction of a patient's head. This measurement may be done by targeting physical features of the patient, like the head, nose, mouth, or eyes; but also by determining the angle of the patient's face, or by any other suitable means. Accordingly, the facing or positioning measuring mechanism may consist of a positioning sensor 227, webcam 202, CMUcam 203, traditional camera, thermal imaging camera, sonar frequency sensor, color-to-frequency sensing detector, pressure sensitive pad, thermal sensors, or any other suitable detection means. In an embodiment, the facing or positioning measuring mechanisms may generally be placed at top center of an integration center 104 as shown in FIGS. 1-9, or on the hood of a system such as shown in FIGS. 1-9 where no specific embodiment of an integration center exists. In other embodiments, facing or position measuring mechanisms may be placed at positions along a structure such as top structural member 108 of FIGS. 1-9, or base support member 114 as shown in FIGS. 1-9. Further, in still other embodiments, facing or positioning measuring mechanisms may be embedded within any portion of an optional hood 102 as shown in FIGS. 1-9, or extend outward beyond the plane 131 of hood 102.

Patient facing or positioning monitoring is useful not only in determining the location of the patient's head for efficient oxygen delivery or delivery of other therapeutic gases, but can also be used to signal to the patient's guardians, caregivers, or other overseers, if the patient has moved outside of hood 102 or gas distribution system 106 as shown in FIGS. 1-9. Indicators can include an LCD or other suitable display 228 as shown in FIGS. 10*a-c*, or an alarm 232 as shown in FIGS.

10a-c, or a remote monitoring subsystem which may be wireless. The signal used to alert a guardian, caregiver, or other overseer, can be some sensory signal, for example, an audible, visual, physical, or the like, or some combination thereof.

In some embodiments, referring generally to FIGS. 10a-10c, additional determinations including oxygen saturation or oxygen prevalence measured via pulse oximeter 216 are made and factored into system behavior. For example, if pulse oximeter 216 measures the patient's oxygen saturation as being too high, less oxygen will be dispersed by the gas distribution system 206, which can either turn off or reduce flow through individual gas distribution ports, or less oxygen will be disbursed by reducing flow from an oxygen source such as a tank or oxygen concentrator. Conversely, if pulse oximeter 216 measures the patient's oxygen saturation as being too low, more oxygen can be disbursed by the same control means.

Similarly, in other embodiments, if overall oxygen prevalence, as measured by oxygen sensor 220, is too high, less oxygen will be dispersed by the gas distribution system 206, which can either turn off or reduce flow through individual gas distribution ports, or less oxygen will be disbursed by reducing flow from an oxygen source such as a tank or oxygen concentrator. Likewise, if overall oxygen prevalence as measured by oxygen sensor 220 is too low, oxygen prevalence can be increased by the same control means.

In some embodiments, should carbon dioxide levels, as measured by carbon dioxide sensor 218 become too high, an emergency flush may be made using the gas distribution system 206. Carbon dioxide sensor 218 may also force alarm 232 to alert the patient, caregiver, or guardian through a controller 229.

Some embodiments may further include a monitoring subsystem, not shown, whereby displays, signals, or system indications are sent to a separate, remote device. This may include a visual display of the patient and system, sound indications conveying status, or any combination thereof. As such, the monitoring subsystem may generally contain one or more cameras, and the remote device may contain an LCD display similar to LCD display 228, and capabilities for sound including speakers and alarm mechanisms.

Various embodiments of systems, devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, feature locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A respiratory treatment system comprising a gas distribution system; and
   at least one sensor, the at least one sensor capable of detecting the orientation of a patient's face,
   wherein said gas distribution system controls an orientation of gas flow to the patients face in part or in whole by direct or indirect response to input from said at least one sensor.

2. The respiratory treatment system of claim 1, wherein said at least one sensor comprises a camera.

3. The respiratory treatment system of claim 1, further comprising an oxygen sensor, wherein said gas distribution system is further controlled by said oxygen sensor.

4. The respiratory treatment system of claim 1, further comprising a blood oximeter, wherein said gas distribution system is further controlled by said blood oximeter.

5. The respiratory treatment system of claim 1, further comprising a hood capable of at least partially confining gases around said patient.

6. The respiratory treatment system of claim 5, wherein said gas distribution system comprises at least one gas delivery port, the at least one gas delivery port mounted to said hood.

7. A respiratory treatment system comprising: a gas distribution system;
   at least one sensor;
   wherein said gas distribution system modifies the orientation of the gas flow contiguous to a patient in direct or indirect response to input from said sensor;
   a mechanism for creating at least one stream of gas;
   a mechanism for altering the direction of said at least one stream of gas;
   wherein said at least one sensor detects at least the orientation of said patient's head, and wherein the orientation of said gas flow contiguous to said patient is modified by altering the direction of at least one stream of gas towards said patient's head.

8. The respiratory treatment system of claim 7, wherein said gas distribution system comprises at least two groups including a first and a second group of gas delivery ports comprising at least one gas delivery port, wherein the orientation of said gas flow contiguous to a patient is modifiable by altering the volume of gas which flows through the first group of gas delivery ports relative to the volume of gas which flows through the second group of gas delivery ports.

9. The respiratory treatment system of claim 7, further comprising at least one sensor configured to detect at least a location of said patient's head.

10. The respiratory treatment system of claim 7, wherein said at least one sensor detects at least the orientation of said patient's face.

11. The respiratory treatment system of claim 7, wherein said at least one sensor comprises a camera.

12. The respiratory treatment system of claim 7, further comprising a hood capable of at least partially confining gases around said patient.

13. The respiratory treatment system of claim 12, wherein said gas distribution system comprises at least one gas delivery port, the at least one gas delivery port mounted to said hood.

14. A respiratory treatment system comprising:
    a gas distribution system;

an extendable hood with at least one open plane which can be adjusted between a retracted and extended position, wherein said gas distribution system distributes gas into the at least partially enclosed space formed by said extendable hood; and a sensor capable of determining the orientation of a head of a patient, wherein said gas distribution system is controlled based on direct or indirect input from said sensor.

15. The respiratory treatment system of claim 14, wherein said gas distribution system comprises at least one gas delivery port, wherein at least one gas delivery port is mounted on said extendable hood.

16. The respiratory treatment system of claim 14, wherein said extendable hood comprises:

a base member comprising a first end and a second end;

a top member comprising a first end and a second end wherein said first end of said top member is hingeably connected to said first end of said base member, and said second end of said top member is hingeably connected to said second end of said base member; and a flexible covering member comprising a first edge and a second edge, wherein said first edge is operatively connected to said base member, said second edge is operatively connected to said top member, and a position of said base member relative to a position of said top member forms a partially enclosed space under the flexible covering wherein the position of said top member is altered by movement about the hingeable connections with said base member.

17. The respiratory treatment system of claim 16, wherein said gas distribution system further comprises at least one gas delivery port, wherein the at least one gas delivery port is mounted to said top member.

18. The respiratory treatment system of claim 16, further comprising at least one sensor mounted to said top member.

19. A method of respiratory treatment comprising:
providing at least one sensor; using the at least one sensor to determine the orientation of a patient's head; and
providing a gas distribution system wherein a flow of oxygen or other treatment gas is directed in the direction of said patient's head based, at least in part, on input from the at least one sensor.

20. The method of claim 19, further comprising determining a location of the patient's head.

21. The method of claim 19, wherein determining the orientation of the patient's head comprises detecting the orientation of the patient's face.

22. The method of claim 19, wherein directing the flow of oxygen or other treatment gas towards a patient's head comprises selectively altering the flow of gas in each of a plurality of gas distribution ports.

* * * * *